(12) United States Patent
Schroën et al.

(10) Patent No.: US 8,481,435 B2
(45) Date of Patent: Jul. 9, 2013

(54) PROTEIN REPELLING SILICON AND GERMANIUM SURFACES

(75) Inventors: Catharina Gerarda Petronella Henrica Schroën, Heelsum (NL); Michel Rosso, Leiden (NL); Johannes Teunis Zuilhof, Bennekom (NL)

(73) Assignee: Wageningen University, Wageningen (NL)

(*) Notice: Subject to any disclaimer, the term of this patent is extended or adjusted under 35 U.S.C. 154(b) by 389 days.

(21) Appl. No.: 12/671,342

(22) PCT Filed: Jul. 31, 2008

(86) PCT No.: PCT/NL2008/050526
§ 371 (c)(1),
(2), (4) Date: Apr. 2, 2010

(87) PCT Pub. No.: WO2009/017411
PCT Pub. Date: Feb. 5, 2009

(65) Prior Publication Data
US 2010/0200963 A1 Aug. 12, 2010

(30) Foreign Application Priority Data
Aug. 1, 2007 (EP) .................................... 07113632

(51) Int. Cl.
*H01L 21/31* (2006.01)
*H01L 21/469* (2006.01)

(52) U.S. Cl.
USPC ...... 438/780; 257/E21.215; 528/10; 436/527; 428/446

(58) Field of Classification Search
None
See application file for complete search history.

(56) References Cited

U.S. PATENT DOCUMENTS

| 6,358,613 | B1 | 3/2002 | Buriak |
| 6,569,979 | B1 * | 5/2003 | Strother et al. ............... 528/10 |
| 7,247,384 | B2 | 7/2007 | Cai et al. |
| 7,285,674 | B2 | 10/2007 | Palma et al. |
| 7,919,046 | B2 | 4/2011 | Delapierre et al. |

(Continued)

FOREIGN PATENT DOCUMENTS

| KR | 20030054809 A | 7/2003 |
| WO | WO 02/19407 A | 3/2002 |

(Continued)

OTHER PUBLICATIONS

Coffinier et al. "Covalent functionalization of silicon nitride surfaces by semicarbazide group" Surface science 601, (2007), pp. 5492-5498.*

(Continued)

*Primary Examiner* — Michelle Mandala
*Assistant Examiner* — Shaka White
(74) *Attorney, Agent, or Firm* — Gilberto M. Villacorta; Sunit Talapatra; Foley & Lardner LLP

(57) ABSTRACT

The present invention relates to a process for preparing a functionalized Si/Ge-surface, wherein an unfunctionalised Si/Ge-surface is contacted in the presence of ultraviolet radiation with a $C_2$-$C_{50}$ alkene and/or a $C_2$-$C_{50}$ alkyne, the alkene and/or alkyne being optionally substituted and/or being optionally interrupted by one or more heteroatoms. The present invention further relates to articles or substrates comprising the functionalized Si/Ge-surface and the use of the functionalised Si/Ge-surface to prevent or to reduce adsorption of a biomolecule to an article or a substrate.

3 Claims, 3 Drawing Sheets

U.S. PATENT DOCUMENTS

2004/0213910 A1* 10/2004 Cai et al. .................. 427/299
2006/0134656 A1   6/2006 Hamers
2006/0234269 A1* 10/2006 Asplund et al. ............... 435/6

FOREIGN PATENT DOCUMENTS

| WO | WO 02/20179 A | 3/2002 |
|----|---|---|
| WO | WO 02/47121 A | 6/2002 |
| WO | WO 02/066162 A | 8/2002 |
| WO | WO 2005/001461 A | 1/2005 |
| WO | WO 2005/123273 A | 12/2005 |
| WO | WO 2005123273 A1 * | 12/2005 |
| WO | WO-2007/048924 A1 | 5/2007 |

OTHER PUBLICATIONS

Coffinier et al: "Covalent functionalization of silicon nitride surfaces by semi carbazide group" Surface Science, vol. 601, No. 23, Nov. 22, 2007, pp. 5492-5498.

Arafat A et al: "Covalent biofunctionalization of silicon nitride surfaces" Langmuir, vol. 23, No. 11, May 22, 2007, pp. 6233-6244.

Arafat A et al: "Tailor-made functionalization of silicon nitride surfaces,"Journal of the American Chemical Society vol. 126, No. 28, Jul. 21, 2004, pp. 8600-8601.

International Search Report corresponding to PCT/NL2008/050526, dated Sep. 22, 2008, 3 pages.

* cited by examiner

PROTEIN REPELLING SILICON AND GERMANIUM SURFACES

CROSS-REFERENCE TO RELATED APPLICATIONS

This application is a National Stage application of PCT/NL2008/050526, filed Jul. 31, 2008, which claims the benefit and priority of European Patent Application No. 07113632.9, filed Aug. 1, 2007. The foregoing applications are incorporated by reference herein in their entirety.

FIELD OF THE INVENTION

The present invention relates to functionalised silicon and germanium surfaces, denoted in this document as Si/Ge-surfaces, a process for functionalising silicon and germanium surfaces and the use thereof for functionalised silicon and germanium surfaces.

BACKGROUND OF THE INVENTION

Several methods have been developed over the last decades to attach organic mono-layers on semi-conductors surfaces. Silicon has been the most widely investigated: especially, stable and densely packed mono-layers were obtained from alkenes and alkynes on hydrogen-terminated surfaces through the use of thermal conditions and photochemical reactions with UV or visible light. Stable and densely packed mono-layers are formed with these methods, opening applications in molecular electronics and sensors.

Since silicon carbide possesses properties intermediate to silicon (composition, energy band gap), mono-layer formation is possible on silicon carbide surfaces similar to silicon surfaces. Silicon carbide has been pursued for high power, high voltage applications, membrane purposes and for sensing in harsh environments.

Silicon-rich silicon nitride ($Si_xN_4$) is also an interesting substrate regarding the formation of organic mono-layers, as it is widely used as insulator for microelectronics and micro-system coatings. Films of this material inhibit diffusion of water, oxygen, and sodium ions, and are widely used as a passivation layer in integrated circuits. Its popularity is mainly motivated by its superior physical and chemical inertness, as it provides an excellent alternative to silicon dioxide in microelectronic and membrane applications.

Polyethylene oxide modifications of surfaces have been used to provide protein repellent ability to those surfaces. For example, US 2005255514, incorporated by reference herein, discloses substrates such as silicon, glass, silica, quartz and metal oxide which are functionalised with a silane having an oligoethylene oxide group to provide protein-resistance.

U.S. Pat. No. 6,358,613, incorporated by reference herein, discloses a method for forming a covalently bound mono-layer on silicon surfaces comprising contacting a silicon substrate with an alkene or alkyne in the presence of a solvent-soluble Lewis acid.

U.S. Pat. No. 6,569,979, incorporated by reference herein, points in detail to the relevance of surfaces that are suitable for immobilization of biologically active materials such as RNA, DNA and fragments or derivatives thereof. U.S. Pat. No. 6,569,979 further discloses a method for modifying a non-oxidized silicon (001) surface, wherein functionalized 1-alkenes, in the absence of any intervening oxygen atoms, are reacted with hydrogen-terminated silicon under UV initiation. However, the method provides modified surfaces having a poor hydrophobicity as appears from the relatively low water contact angles. Modification by using tert.-butoxycarbonyl protected 10-amino-1-decene afforded a modified non-oxidized silicon (001) surface having a water contact angle θ of only 78.1°, i.e. near-identical to the value of non-modified hydrogen-terminated Si(001).

WO 02/19407, incorporated by reference herein, also discloses a method for covalently binding a functionalised alkene to a surface comprising hydrogen terminated silicon or hydrogen terminated germanium.

WO 02/66162, incorporated by reference herein, discloses a method for functionalising hydrogen terminated silicon surfaces with functionalised alkynes.

Korean patent application KR 2003/0054809, incorporated by reference herein, discloses a method for functionalising of hydrogen terminated silicon with w-amino alkenes in the presence of a radical initiator such as AIBN (azobisisobutyronitril) by irradiation with UV or by heating at 20°-150° C.

US 2004/213910, incorporated by reference herein, discloses a method for functionalising hydrogen terminated silicon surfaces with ω-(ethylene glycol oligomer)-alkenes by irradiation with UV.

US 2006/0134656, incorporated by reference herein, discloses a method for functionalising of hydrogen terminated silicon or carbon surfaces with ω-(ethylene glycol oligomer)-alkenes by irradiation with UV.

WO 2005/001461, incorporated by reference herein, also discloses a method for functionalising hydrogen terminated silicon surfaces with alkenes or alkynes.

WO 2005123273, incorporated by reference herein, discloses functionalized silicon and/or germanium surfaces, methods for the preparation of such functionalized silicon and/or germanium surfaces, the use of such functionalized silicon and/or germanium surfaces for the preparation of surface-bonded organic materials and the use thereof in industrial devices. The silicon and/or germanium surfaces comprise silicon nitride and silicon carbide, germanium nitride and germanium carbide, and silicon germanium surfaces.

WO 2007048924, incorporated by reference herein, discloses a method for grafting molecules of interest on a silicon substrate via a spacer compound, said grafting including at least one click chemistry reaction to the supports thus obtained as well as their uses in nanotechnologies and nanobiotechnologies, such as molecular electronics, the manufacture of biochips or of sensors.

Consequently, the prior art discloses methods for functionalising hydrogen terminated silicon, germanium and carbon surfaces with functionalised alkenes and alkynes. These functionalised surfaces have the disadvantage that they are not very stable. In addition, some methods of the prior art apply elevated temperatures (optionally in combination with UV-irradiation) which is detrimental to the homogeneity of the functionalisation and to the integrity of certain functionalised alkenes and alkynes.

SUMMARY OF THE INVENTION

The present invention relates to a functionalised Si/Ge-surface, wherein $C_1$-$C_{50}$ alkyl or $C_2$-$C_{50}$ alkenyl groups are covalently bonded to an unfunctionalised Si/Ge-surface, the alkyl and alkenyl groups being optionally substituted and/or being optionally interrupted by one or more heteroatoms.

The present invention further relates to a process for preparing a functionalized Si/Ge-surface, wherein an unfunctionalised Si/Ge-surface is contacted in the presence of ultra-violet radiation with a $C_2$-$C_{50}$ alkene and/or a $C_2$-$C_{50}$ alkyne, the alkyl or alkenyl groups being optionally substituted and/or being optionally interrupted by one or more heteroatoms.

Additionally, the present invention relates to an article or a substrate comprising the functionalized Si/Ge-surface and to the use of the functionalised Si/Ge-surface to prevent or to reduce adsorption of a biomolecule to an article or a substrate.

DETAILED DESCRIPTION OF THE INVENTION

Definitions

Figure 1:
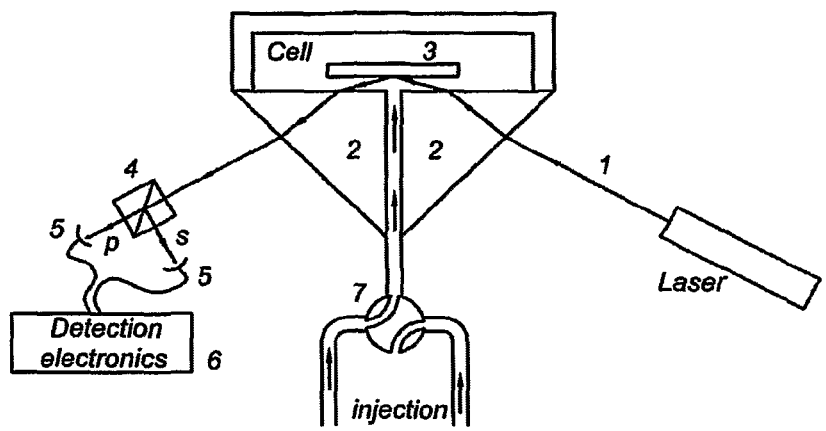
FIG. 1 shows a schematic representation of a reflectometer as used in the experiments that are described in the examples.

The verb "to comprise" as is used in this description and in the claims and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

A biomolecule is herein defined as a substance that has a biological effect or response, e.g. a therapeutic, a prophylactic, a probiotic, or an immunising effect, when it is administered to a living organism (in particular a vertebrate) or when a living organism is exposed in some way to the biomolecule. Examples of such biomolecules include proteins and (poly) peptides (synthetic and natural), peptide mimetics, hormones (peptide, steroid and corticosteroid), D and L amino acid polymers, oligosaccharides, polysaccharides, nucleotides, oligonucleotides and nucleic acids, including DNA and RNA, and protein nucleic acid hybrids including PNA. According to the present invention, the biomolecule is preferably a protein.

Unsubstituted alkyl groups have the general formula $C_nH_{2n+1}$ and may be linear, branched or cyclic. Optionally, the alkyl groups are substituted by one or more substituents further specified in this document. Examples of suitable alkyl groups include methyl, ethyl, 2-propyl, 1-hexyl, 1-dodecyl and the like.

Unsubstituted alkenyl groups have the general formula $C_nH_{2n-1}$. Examples of suitable alkenyl groups are ethenyl, propenyl, butenyl, pentenyl, decenyl, octadecenyl, and eicosenyl and the like.

Aryl groups comprise at least six carbon toms and may include monocyclic and bicyclic structures. Optionally, the aryl groups may be substituted by one or more substituents further specified in this document. Examples of aryl groups include groups such as phenyl, naphtyl, and the like.

Arylalkyl groups and alkaryl groups comprise at least seven carbon atoms and may include monocyclic and bicyclic structures. Optionally, the aryl groups may be substituted by one or more substituents further specified in this document. An arylalkyl group includes benzyl and the like. An alkylaryl group is for example 4-t-butylphenyl and the like.

Where the aryl groups, arylalkyl and alkaryl are denoted as (hetero)aryl groups, alk(hetero)aryl or (hetero)arylalkyl groups, the heteroaryl group comprises one to four heteroatoms selected from the group consisting of oxygen, nitrogen, and sulphur.

Unsubstituted alkenes have the general formula $C_nH_{2n}$ whereas unsubstituted alkynes have the general formula $C_nH_{2n-2}$.

The Functionalized Si/Ge-Surfaces

According to a first preferred embodiment of the present invention, the $C_1$-$C_{50}$ alkyl and $C_2$-$C_{50}$ alkenyl groups which are covalently bonded to the Si/Ge-surfaces may be linear, branched, or cyclic. The $C_1$-$C_{50}$ alkyl or $C_2$-$C_{50}$ alkenyl groups may be further substituted with one or more, optionally masked or protected, functional groups P selected from the group consisting of hydrogen, —CH=CH($R^1$)$_2$, —C≡C$R^1$, halogen (preferably Cl, Br or I), —CN, —NCX, —XCN, —X$R^1$, —N($R^1$)$_2$, —$^+$N($R^1$)$_3$, —CN, —C(X) N($R^1$)$_2$, —C(X)$R^1$, —C(X)X$R^1$, —S(O)$R^1$, —S(O)$_2R^1$, —S(O)O$R^1$, —S(O)$_2$O$R^1$, —S(O)N($R^1$)$_2$, —S(O)$_2$N($R^1$)$_2$, —OS(O)$R^1$, —OS(O)$_2R^1$, —OS(O)O$R^1$, —OS(O)$_2$O$R^1$, —P(O)($R^1$)(O$R^1$), —P(O)(O$R^1$)$_2$, —OP(O)(O$R^1$)$_2$, —Si($R^1$)$_3$, —XC(X)$R^1$, —XC(X)X$R^1$, —XC(X)N($R^1$)$_2$, —N($R^1$)C(X)$R^1$, —N($R^1$)C(X)X$R^1$, and —N($R^1$)C(X)N ($R^1$)$_2$, wherein X is oxygen or sulphur and wherein all $R^1$ substituents are independently selected from the group consisting of hydrogen, $C_1$-$C_{24}$ alkyl groups, $C_6$-$C_{24}$ (hetero)aryl groups, $C_7$-$C_{24}$ alk(hetero)aryl groups and $C_7$-$C_{24}$ (hetero) arylalkyl groups. The alkyl groups, (hetero)aryl groups, alk (hetero)aryl groups, and (hetero)arylalkyl groups defined for $R^1$ may be substituted with a substituent P as enumerated for the $C_1$-$C_{50}$ alkyl and $C_2$-$C_{50}$ alkenyl groups.

If the $C_1$-$C_{50}$ alkyl or $C_2$-$C_{50}$ alkenyl groups are substituted with one or more substituents P, it is preferred that at least one substituent P is at the co-position of the $C_1$-$C_{50}$ alkyl or $C_2$-$C_{50}$ alkenyl groups. Most preferably, the $C_1$-$C_{50}$ alkyl or $C_2$-$C_{50}$ alkenyl groups are substituted with one substituent P at their ω-position.

It is furthermore preferred that the $C_2$-$C_{50}$ alkenyl groups are 1-alkenyl groups.

According to another preferred embodiment of the present invention, the $C_1$-$C_{50}$ alkyl and $C_2$-$C_{50}$ alkenyl groups may also be interrupted by one or more heteroatoms which are preferably selected from the group consisting of oxygen, sulphur, and nitrogen, most preferably oxygen. A preferred group of such $C_1$-$C_{50}$ alkyl and $C_2$-$C_{50}$ alkenyl groups that are interrupted by one or more heteroatoms is represented by Formula (I):

-A-B—C    (I)

wherein:
A is a linear, branched or cyclic, optionally substituted alkylene group having 2 to 24 carbon atoms or a linear, branched or cyclic, optionally substituted alkenylene group having 2 to 24 carbon atoms, the alkenylene group being a 1-alkenylene or an internal alkenylene group, preferably a 1-alkenylene;

B is a —[X-D-X]$_n$— group, wherein all X groups are independently selected from the group consisting of —O—, —S— and —N($R^1$)— (wherein $R^1$ is selected from the group consisting of hydrogen, $C_1$-$C_{24}$ alkyl groups, $C_6$-$C_{24}$ (hetero)aryl groups, $C_7$-$C_{24}$ alk(hetero)aryl groups and $C_7$-$C_{24}$ (hetero)arylalkyl groups as defined above), D represents an (optionally substituted) ethylene group, an (optionally substituted) propylene group, or a mixture thereof (wherein the ethylene groups and propylene groups may be substituted with one or more substituents P as enumerated for the $C_1$-$C_{50}$ alkyl and $C_2$-$C_{50}$ alkenyl groups), and n is in the range of 1-100, preferably in the range of 1-50; and C is selected from the group consisting of hydrogen, a linear, branched, or cyclic, optionally substituted $C_1$-$C_{24}$ alkyl group, an optionally substituted $C_6$-$C_{24}$ (hetero)aryl group, an optionally substituted $C_7$-$C_{24}$ (hetero)arylalkyl group and an optionally substituted $C_7$-$C_{24}$ alkyl(hetero)aryl group, wherein the alkyl groups, (hetero)aryl groups, (hetero)arylalkyl groups and alkyl(hetero)aryl groups may be substituted with one or more substituents P as enumerated for the $C_1$-$C_{50}$ alkyl and $C_2$-$C_{50}$ alkenyl groups. Where the aryl group or aryl groups are heteroaryl groups, the heteroaryl group comprises one to four heteroatoms selected from the group consisting of oxygen, nitrogen, and sulphur.

In Formula (I), A is preferably a linear alkylene group having 1 to 24 carbon atoms or a linear alkenylene group having 2 to 24 carbon atoms, wherein the alkenylene group is preferably a 1-alkenylene group. More preferably, A is a linear alkylene group which is preferably unsubstituted.

Most preferably, the $C_1$-$C_{50}$ alkyl group has the Formula (IIA),

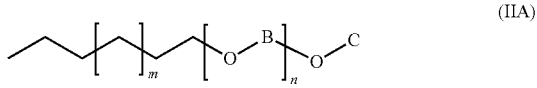

(IIA)

wherein m is in the range of 1 to 50 and n is in the range of 1 to 100 and B and C are as disclosed above. Most preferably, B is an ethylene group. Preferably, C is hydrogen or a linear, branched or cyclic, optionally substituted $C_1$-$C_{24}$ alkyl group, more preferably a linear $C_1$-$C_{24}$ alkyl group, most preferably a methyl group.

Most preferably, the $C_2$-$C_{50}$ alkenyl group has the Formula (IIB):

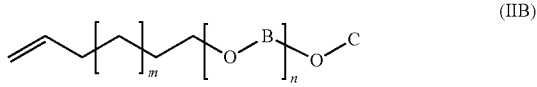

(IIB)

wherein m is in the range of 1 to 50 and n is in the range of 1 to 100 and B and C are as disclosed above. Most preferably, B is an ethylene group. Preferably, C is hydrogen or a linear, branched or cyclic, optionally substituted $C_1$-$C_{24}$ alkyl group, more preferably a linear $C_1$-$C_{24}$ alkyl group, most preferably a methyl group.

According to yet another preferred embodiment of the present invention, the $C_1$-$C_{50}$ alkyl and $C_2$-$C_{50}$ alkenyl groups comprise at least an ethynylene moiety, i.e. that the $C_1$-$C_{50}$ alkyl and $C_2$-$C_{50}$ alkenyl groups are linear groups having 6 to 24 carbon atoms according to Formula (III):

$$—CH_2—CH_2—(CH_2)_p—(C\equiv C)_q—CH_2—P \quad (III)$$

wherein p is in the range of 1 to 7 and q is in the range of 1 to 7, the groups —($CH_2$)— and —(C≡C)— optionally occurring in a random sequence, and wherein P is as defined above. Such ethynylene groups can be polymerized to provide a cross-linked network that will reduce the permeability of the mono-layer, and that will provide more stabilization to the mono-layer. Examples of this linear group are:

$$—(CH_2)_7—C\equiv C—CH_2—C\equiv C—(CH_2)_8—P$$

and $$—(CH_2)_9—C\equiv C—C\equiv C—(CH_2)_9—P$$

Preferably, the linear group has the formula —$CH_2$—$CH_2$—$(CH_2)_p$—$(C\equiv C)_q$—$(CH_2)_r$—P, wherein p is 1 to 9, preferably 7, r is 1 to 9 and q is 1 or 2.

According to yet another embodiment of the present invention, the $C_1$-$C_{50}$ alkyl and $C_2$-$C_{50}$ alkenyl groups are substituted at their ω-position with a group according to Formula (IV) and Formula (V):

(IV)

(V)

or tautomers thereof, wherein $R^2$ is selected from the group consisting of hydrogen, —OH and —$NH_2$; and wherein $R^3$ is selected from the group consisting of the groups mentioned for $R^1$, ethylene oxide propylene oxide polymers according to the formula —B—C defined above, and sugar residues.

Si/Ge-Surfaces

Silicon surfaces are herein generally defined as silicon nitride and silicon carbide. Likewise, germanium surfaces are herein generally defined as germanium nitride and germanium carbide. Although these expressions are apparent to the person skilled in the art, a more specific definition of the silicon surfaces and germanium surfaces are surfaces comprising metal nitrides according to the general formula $M_xN_4$, wherein M is Si, Ge or a mixture thereof, x is in the range of about 3 to about 6, preferably 3 to 4, metal carbides according to the general formula $M_xC_y$, wherein M is Si, Ge or a mixture thereof, x is in the range of about 0.3y to about 3y, as well as "strained silicon" which is known in the art as $Si_{1-x}Ge_x$ wherein x is in the range of about 0 to about 1, preferably about 0.01 to about 1, more preferably about 0.05 to about 0.95. It is well known in the art that the stoichiometry of these surfaces can continuously be varied, depending on the properties desired. In this document, the silicon surface and/or the germanium surface is referred to for brevity as a "Si/Ge-surface".

"Strained silicon" comprises germanium atoms in the crystal lattice with the result that the atoms are spread further apart than in neat silicon. In strained silicon, electrons experience less resistance and flow up to 70 percent faster compared to neat silicon which can lead to much faster chips. Strained silicon and methods of preparing strained silicon is for example disclosed in U.S. Pat. No. 6,464,780 and US 20040087119, both incorporated by reference herein.

Mono-Layer Formation

According to the present invention, the functionalised Si/Ge-surfaces are functionalised by contacting an unfunctionalised Si/Ge-surface in the presence of ultraviolet radiation with a $C_2$-$C_{50}$ alkene and/or a $C_2$-$C_{50}$ alkyne, preferably a 1-$C_2$-$C_{50}$ alkene and/or a 1-$C_2$-$C_{50}$ alkyne (i.e. a terminal alkene or a terminal alkyne), the alkene and/or alkyne being optionally substituted and/or being optionally interrupted by one or more heteroatoms, preferably 1 to 10 heteroatoms, said heteroatoms being selected from the group consisting of O, S and $NR^1$; the heteroatom is most preferably O.

The $C_2$-$C_{50}$ alkene and/or a $C_2$-$C_{50}$ alkyne are further optionally substituted with one or more, optionally masked or protected, functional groups P selected from the group consisting of hydrogen, —CH=CH($R^1$)$_2$, —C≡$CR^1$, halogen (preferably Cl, Br or I), —CN, —NCX, —XCN, —$XR^1$, —N($R^1$)$_2$, —$^+$N($R^1$)$_3$, —CN, —C(X)N($R^1$)$_2$, —C(X)$R^1$, —C(X)$XR^1$, —S(O)$R^1$, —S(O)$_2R^1$, —S(O)$OR^1$, —S(O)$_2OR^1$, —OS(O)$R^1$, —OS(O)$_2R^1$, —OS(O)$OR^1$, —OS(O)$_2OR^1$, —S(O)N($R^1$)$_2$, —S(O)$_2$N($R^1$)$_2$, —P(O)($R^1$)($OR^1$), —P(O)($OR^1$)$_2$, —OP(O)($OR^1$)$_2$, —Si($R^1$)$_3$, —XC(X)$R^1$, —XC(X)$XR^1$, —XC(X)N($R^1$)$_2$, —N($R^1$)C(X)$R^1$, —N($R^1$)C(X)$XR^1$, and —N($R^1$)C(X)N($R^1$)$_2$, wherein X is oxygen or sulphur, and wherein all $R^1$ substituents are independently selected from the group consisting of hydrogen, alkyl groups, (hetero)aryl groups, alk(hetero)aryl groups and (hetero)arylalkyl groups. The alkyl groups, (hetero)aryl groups, alk(hetero)aryl groups, and (hetero)arylalkyl groups are as defined above.

According to another preferred embodiment of the present invention, the $C_2$-$C_{50}$ alkene and/or a $C_2$-$C_{50}$ alkyne may also be interrupted by one or more heteroatoms which are preferably selected from the group consisting of oxygen, sulphur, and nitrogen. A preferred group of such $C_2$-$C_{50}$ alkenes and $C_2$-$C_{50}$ alkynes are represented by Formula (VI):

$$\text{E-A-B—C} \qquad (VI)$$

wherein A, B and C are as defined above and E is a group according to Formula (VII):

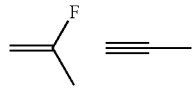

(VII)

wherein F is hydrogen or a linear $C_1$-$C_6$ alkyl group.

In Formula (VI), A is preferably a linear alkylene group having 2 to 24 carbon atoms. More preferably, A is unsubstituted.

Most preferably, the $C_2$-$C_{50}$ alkene has the Formula (VIII),

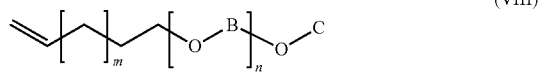

(VIII)

wherein m is in the range of 1 to 50 and n is in the range of 1 to 100 and B and C are as disclosed above. Most preferably, B is an ethylene group. Preferably, C is hydrogen or a linear, branched or cyclic, optionally substituted $C_1$-$C_{24}$ alkyl group, more preferably a linear $C_1$-$C_{24}$ alkyl group, most preferably a methyl group.

Most preferably, the $C_2$-$C_{50}$ alkyne has the Formula (IX):

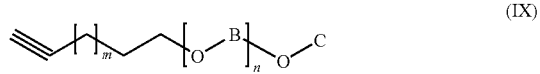

(IX)

wherein m is in the range of 1 to 50 and n is in the range of 1 to 100 and B and C are as disclosed above. Most preferably, B is an ethylene group. Preferably, C is hydrogen or a linear, branched or cyclic, optionally substituted $C_1$-$C_{24}$ alkyl group, more preferably a linear $C_1$-$C_{24}$ alkyl group, most preferably a methyl group.

According to yet another preferred embodiment of the present invention, the $C_1$-$C_{50}$ alkene and $C_2$-$C_{50}$ alkyne comprise at least an ethynylene moiety, i.e. that the $C_1$-$C_{50}$ alkene and $C_2$-$C_{50}$ alkyne have 6 to 24 carbon atoms according to Formulas (X) and (XI):

$$CH=CH—(CH_2)_p—(C≡C)_q—CH_2—P \qquad (X)$$

$$C≡C—(CH_2)_p—(C≡C)_q—CH_2—P \qquad (XI)$$

wherein p is in the range of 1 to 7 and q is in the range of 1 to 7, the groups —(CH$_2$)— and —(C≡C)— optionally occurring in a random sequence, and wherein P is as defined above.

Preferably, the linear group has the formula —CH$_2$—CH$_2$—(CH$_2$)$_p$—(C≡C)$_q$—(CH$_2$)$_r$—P, wherein p is 1 to 9, preferably 7, r is 1 to 9 and q is 1 or 2.

According to yet another embodiment of the present invention, the $C_1$-$C_{50}$ alkene and $C_2$-$C_{50}$ alkyne are substituted at their co-position with a group according to Formula (IV) and Formula (V):

(IV)

(V)

or tautomers thereof, wherein $R^2$ is selected from the group consisting of hydrogen, —OH and —NH$_2$; and wherein $R^3$ is selected from the group consisting of the groups mentioned for $R^1$, ethylene oxide propylene oxide polymers according to the formula —B—C defined above, and sugar residues.

According to the present invention, it is preferred that the ultraviolet radiation has a wave length of 250 to 300 nm, more preferably of 250 nm to 285 nm.

According to the present invention, the process is preferably performed at a temperature of 0° to 50° C., more preferably 15° to 30° C. and most preferably at ambient temperature (15° to 25° C.).

Applications

The present invention also relates to articles and substrates comprising the functionalized Si/Ge-surface, in particular where protein contamination needs to be prevented or reduced. Such articles include in particular micro-sieves which are for example used in dairy food processing, as coatings for packaging materials, surgical devices such as implants, drains, tubes, stents, diagnostic devices, bioanalytical devices such as biosensors, biochips, devices for the sustained release of pharmaceuticals, and the like. Micro-sieves are well known in the art and are a type of microperforated membrane which are e.g. prepared from silicon wafers by UV laser interference lithography and coated with silicon-rich silicon nitride ($Si_xN_4$, x≈4; cf. C. J. M. van Rijn, "Nano and Micro Engineered Membrane Technology", Elsevier Science Publishers (2004)).

EXAMPLES

1-Decene (>97%), 1-dodecene (>99%), 1-tetradecene (>97%), 1-hexadecene (99%), undec-10-eneoic acid (98%), and methyl 10-undecenoate (96%) were purchased at Sigma-Aldrich and distilled twice under reduced pressure before use. 1-Octadecene (>95%, Sigma-Aldrich) and 1-docosene (>99%, TCI Europe) were recrystallised twice at 4° C. in ethyl acetate with ethanol as anti-solvent. 2,2,2-Trifluoroethyl 10-undecenoate and 11-fluoroundecene were synthesized according to L. C. P. de Smet et al., Appl. Surf. Sci. 2005, 252 (1), 24-30 and Q.-Y. Sun et al., J. Am. Chem. Soc. 2005, 127(8), 2514-2523, respectively.

Mono-Layer Formation—General Procedure

Silicon carbide (SiC) and silicon nitride ($Si_xN_4$) samples (1×1 $cm^2$ or 3×1.5 $cm^2$ for IRRAS) were cleaned first by sonication in acetone, followed by oxidation in piranha solution ($H_2SO_4$ and 33% $H_2O_2$:3/1) at 90° C. for 10 min and wet-etching of the native silicon oxide with a 2.5% solution of HF for 2 min. Right after this step, wafers were dipped into argon-saturated neat alkenes, in quartz or glass flasks. After 30 more min.

under argon, the 25 Watt pen lamps (Jelight Corporation, Irvine, Calif., USA) were placed at 4 mm from the surface and turned on for the desired time. At the end of the experiment, samples were removed and rinsed several times with petroleum ether, ethanol, and dichloromethane, and sonicated in the same solvents. The functionalisation was performed on 3 different SiC surfaces: polished Si-rich and C-rich surfaces of 6H-SiC substrate from TDI USA, and polycrystalline 3C-SiC films (thickness: 250 nm) obtained by chemical vapour deposition on Si(100). Overall, polished 6H-SiC surfaces (both C-face and Si-face) give similar results to the polycrystalline films (poly-SiC).

Static Water Contact Angle

Silicon carbide surfaces were characterised by static water contact angle measurements performed using an Erma Contact Angle Meter G-1 (volume of the drop of demineralized water=3.5 μl).

X-Ray Photoelectron Spectroscopy (XPS)

The XPS analysis was performed using a JPS-9200 Photoelectron Spectrometer (JEOL, Japan). The high-resolution spectra were obtained under UHV conditions using monochromatic Al Kα X-ray radiation at 12 kV and 25 mA, using an analyser pass energy of 10 eV. High-resolution spectra were corrected with a linear background before fitting.

Fourier Transform Infrared Reflection Absorption Spectroscopy (FT-IRRAS)

Spectra were measured with a Bruker Tensor 27 FT-IR spectrometer, using a commercial variable-angle reflection unit (Auto Seagull, Harrick Scientific). A Harrick grid polarizer was installed in front of the detector, and was used for measuring spectra with p-polarized (parallel) radiation with respect to the plane of incidence at the sample surface. Single channel transmittance spectra were collected using a spectral resolution of 4 $cm^{-1}$, using 1024 scans in each measurement. The optimal angle for data collection was found to be 68°. All the reported measurements were performed at this angle. Raw data files were divided by data recorded on a plasma-oxidized reference SiC, to give the reported spectra.

Atomic Force Microscopy (AFM)

Images were obtained with an MFP-3D AFM from Asylum Research (Santa Barbara, Calif.). Imaging was performed in AC mode in air using OMCL-AC240 silicon cantilevers (Olympus Corporation, Japan).

Reflectometry

A schematic representation of a reflectometer is shown in FIG. 1, wherein (1) is the reflectometer cell, (2) represents the detection electronics, (3) the laser and (4) the injection device. In this reflectometer, monochromatic light (1) (He—Ne laser; 632.8 nm) is linearly polarized and passes a 45° glass prism (2). This beam arrives at the interface (3) with an angle of incidence close to the Brewster angle (θ=arc tan n2/n1) for the solvent/substrate interface. After reflection at the interface and refraction at the prism, the beam is split into its p- and s-polarized components, relative to the plane of incidence by means of a beam splitter (4). Both components are detected separately by two photodiodes (5) and the ratio between the intensity of the parallel and perpendicular components is the output signal S (=Ip/Is) (the output-signal given by the detection box is 10×S). It is combined with a stagnant point flow cell, allowing the introduction of buffer or protein solutions, to study homogeneous adsorption on surfaces in diffusion-controlled conditions.

Bovine serum albumin (BSA) and Fibrinogen (FBI) solutions (0.1 mg/L) were freshly prepared in PBS buffer (pH 6.75, ionic strength 0.08 M). All reflectometry experiments were performed at 23° C. Before each experiment, surfaces were incubated at least 1 hour in buffer to avoid any artefacts due to wetting at the beginning of the experiment. After positioning of surfaces, buffer was injected until the output signal S was nearly constant. The signal was considered constant when it did not change more than 0.01 V within a time span of two minutes. Each experiment involved at least one adsorption phase, where protein solutions were injected onto the surface, and one subsequent desorption phase, where only buffer was injected.

Example 1

A silicon carbide surface was provided with a mono-layer of methoxytri(ethylene oxide)undec-10-enyl ether (Formula (VIII), m=7, n=3; EO3) according to the general procedure described above.

Example 2

A silicon carbide surface was provided with a mono-layer of methoxyhexa (ethylene oxide)undec-10-enyl ether (Formula (VIII), m=7, n=6; EO6) according to the general procedure described above.

Example 3

Reflectometry Measurements

Oligoethylene oxide-coated silicon nitride surfaces (SiN-EO3 and SiN-EO6) were prepared according to the general procedure described above. Unmodified surfaces were submitted to protein solutions, and the oxidized surfaces show an adsorption maximum of 1.25±0.05 $mg/m^2$ of BSA and 2.7±0.05 $mg/m^2$ of FBI after about 30 min. On modified surfaces, the adsorption of both proteins is reduced almost to the detection limit of the reflectometry measurement (see above), and this regardless of the time (the measurement was performed up to 3 h on one sample without a visible change in the signal. Compared to oxidized surfaces without oligoethylene oxide coatings, the signal for BSA was reduced to 16 and 7% by EO3 and EO6 coatings, respectively, and FBI adsorption to less than 5% by both types of coatings. During the desorption step with pure buffer, the initial signal for protein-free surfaces was restored, indicating that no adsorption took place.

Example 4

Figure 2:
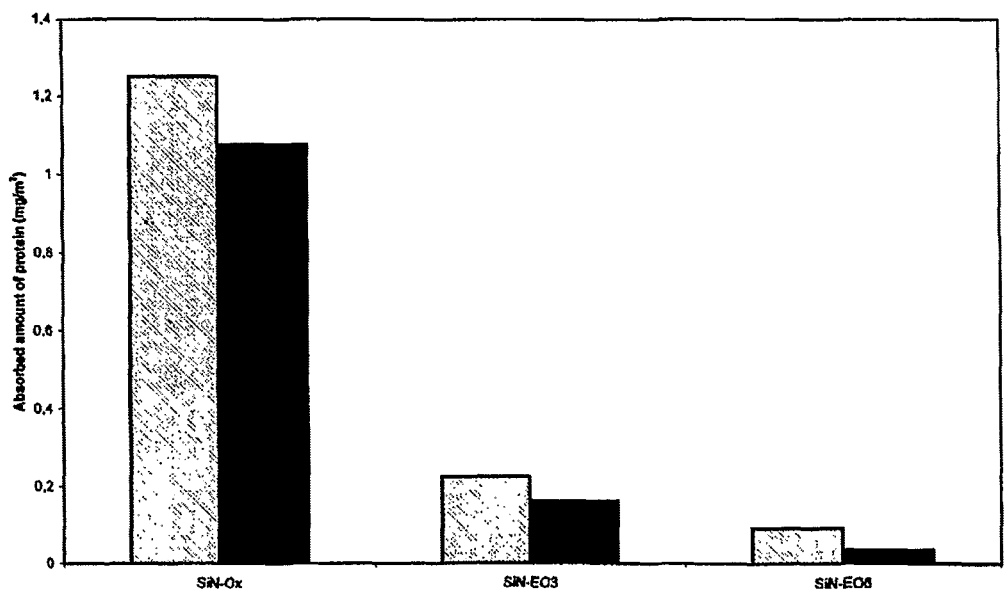
FIG. 2 shows the evolution of static water contact angles θ on functionalised Si/Ge surfaces before and after protein (BSA) adsorption.
Figure 3:
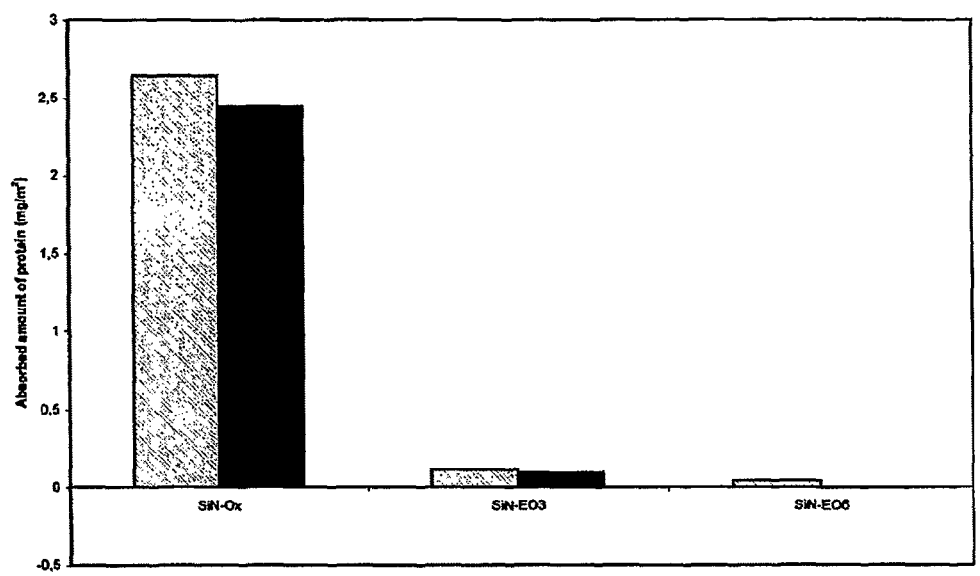
FIG. 3 shows the evolution of static water contact angles θ on functionalised Si/Ge surfaces before and after protein (FBI) adsorption.

The surfaces according to Example 3 were subjected to static water contact angle measurements. A comparison of static water contact angles and AFM before and after reflectometry experiments offer a good confirmation of the performance of these mono-layers. FIGS. 2 and 3 shows the evolution of static water contact angles θ on the same types of surfaces before and after protein adsorption: the uncoated surfaces show a clear change in the wettability of the surfaces after protein adsorption, characteristic of a layer of adsorbed protein, giving a contact angle of 39±2° and 70±5° for BSA (FIG. 2) and FBI (FIG. 3), respectively.

For mono-layer-coated surfaces, having well-defined initial contact angles of 64±1° (EO3) and 58±1° (EO6), the values remain the same after adsorption, showing no adsorption of protein.

Example 5

Figure 4:
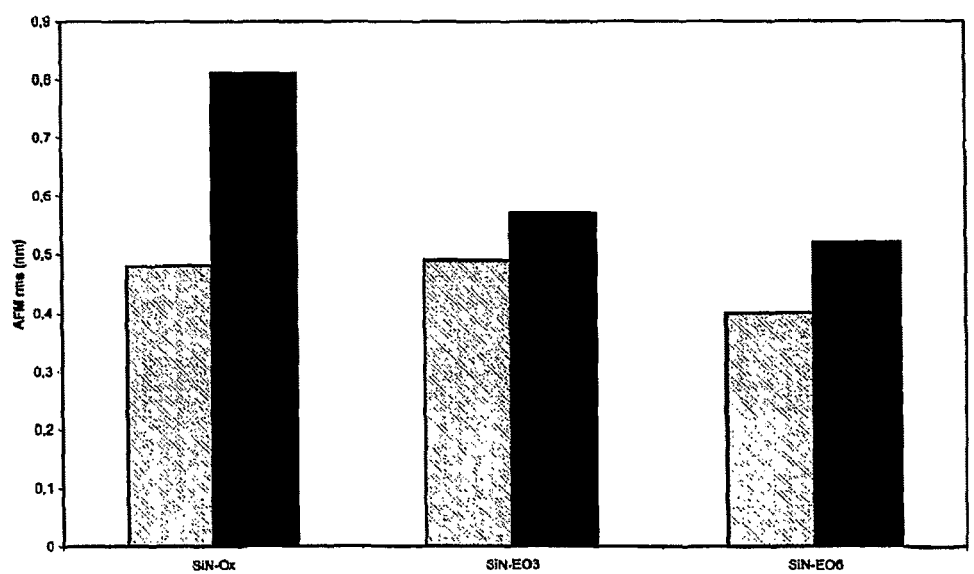
FIG. 4 shows the roughness of samples before (left-hand bar) and after (right-hand bar) exposure of the functiolised Si/Ge-surfaces to protein (BSA) solutions as assessed by AFM measurement.
Figure 5:
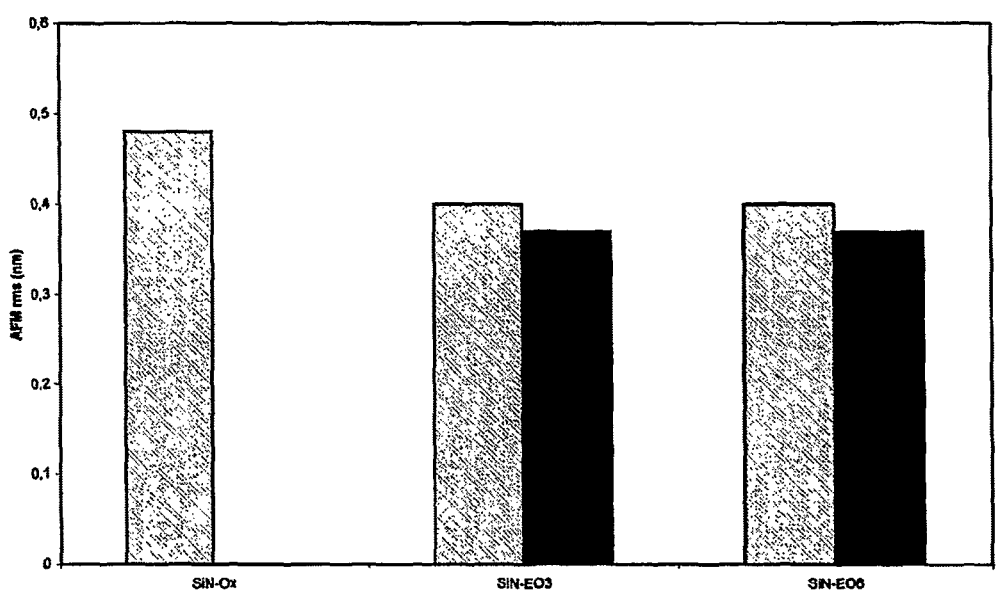
FIG. 5 shows the roughness of samples before (left-hand bar) and after (right-hand bar) exposure of the functiolised Si/Ge-surfaces to protein (FBI) solutions as assessed by AFM measurement.

To evaluate the effect of protein adsorption in another way, the roughness of samples before and after exposure of the surfaces to protein solutions was assessed by AFM measurement. Accordingly, this was done for the surfaces according to Example 3. For both proteins (BSA and FBI) the roughness of unmodified surfaces increases clearly upon adsorption. The rms values of oxidized surfaces change from 0.45 nm to 0.8 nm after adsorption of BSA. Comparatively, for the EO3 and EO6-modified surfaces, only a very small if any increase of the roughness is found. See FIGS. 4 and 5.

Example 6

Polycrystalline 3C-SiC films (thickness 250 nm) obtained by chemical vapour disposition on Si(100) [C. S. Roper, V. Radmilovic, R. T. Howe, R. Maboudian, J. Electrochem. Soc. 153, C562-C566, 2006] were first cleaned by sonication in acetone, followed by oxidation in air-based plasma for 10 minutes and wet-etching of the native silicon oxide with a 2.5% solution of HF for 2 minutes. Right after this step, wafers were placed into heated neat 1-hexadecene at 130° C. under argon atmosphere and left to react for at least 6 h. After this time, samples were removed and rinsed several times with petroleum ether, ethanol and dichloromethane and sonicated in the same solvents. The polycrystalline 3C-SiC films had a root-mean-square roughness of <1 mm (flat surface) or a root-mean-square roughness of ≈120 nm. The water contact angles of the modified surfaces are 110° (flat surface) and 105° (rough surface).

The modified surfaces were exposed to (a) 2 M HCl at 90° C. or (b) 0.001 M NaoH at 60° C. The results after an exposure for 4 h are summarised in Table 1. Similar results were obtained with polished 6H-SiC surfaces (both C-face and Si-face).

TABLE 1

|  | Flat surface Water contact angle (°) | Rough surface Water contact angle (°) |
| --- | --- | --- |
| Untreated | 110 | 105 |
| Treatment (a) | 110 | 97 |
| Treatment (b) | 93 | 88 |

Hence, all samples retained a water contact angle higher than 85° which should be compared with the completely hydrophilic surface (water contact angle <15° C.) of bare hydroxyl-terminated SiC. The stability of the samples under the warm, basic conditions according to treatment (b) is much higher than that of mono-layers of alkenes on silicon nitride surfaces.

Example 7

Polycrystalline 3C-SiC films (thickness 250 nm) were functionalised with several alkenes having different chain length according to the method described in Example 5. The water contact angles are shown in Table 2.

TABLE 2

| Alkene | Water contact angle (°) |
| --- | --- |
| $H_2C=CHC_8H_{17}$ | 95 |
| $H_2C=CHC_{10}H_{21}$ | 101 |
| $H_2C=CHC_{12}H_{25}$ | 106 |
| $H_2C=CHC_{14}H_{29}$ | 106 |
| $H_2C=CHC_{16}H_{33}$ | 107 |
| $H_2C=CHC_{20}H_{41}$ | 105 |

The water contact angles did not change upon sonication in petroleum ether or dichloromethane. The high water contact angles show the formation of hydrophobic mono-layers with an optimal value for alkyl chains containing at least 14 carbon atoms. The high values of the water contact angles approach those observed for highly packed mono-layers such as thiol mono-layers on gold surfaces and alkene mono-layers on H-terminated silicon surfaces.

The invention claimed is:

1. A process for preparing a functionalized Si/Ge-surface, wherein an unfunctionalized Si/Ge-surface is contacted in the presence of ultraviolet radiation with a $C_2$-$C_{50}$ alkene and/or a $C_2$-$C_{50}$ alkyne, the alkene and/or alkyne being optionally substituted and/or being optionally interrupted by one or more heteroatoms, wherein the unfunctionalized Si/Ge-surface is selected from the group consisting of silicon nitride, silicon carbide, germanium nitride, germanium carbide and strained silicon, wherein the $C_2$-$C_{50}$ alkene and/or a $C_2$-$C_{50}$ alkyne are represented by Formula (VI):

E-A-B—C        (VI)

wherein:

A is a linear, branched or cyclic, optionally substituted alkylene, or alkenylene group having 2 to 24 carbon atoms, the alkenylene group being a 1-alkenylene or an internal alkenylene group;

B is a —[X-D-X]$_n$— group, wherein all X groups are independently selected from the group consisting of —O—, —S— and —N(R$^1$)— (wherein R$^1$ is as defined above), D represents an (optionally substituted) ethylene group, an (optionally substituted) propylene group, or a mixture thereof (wherein the ethylene groups and propylene groups may be substituted with one or more substituents P as enumerated for the $C_1$-$C_{50}$ alkyl and $C_2$-$C_{50}$ alkenyl groups), and n is in the range of 1-100;

C is selected from the group consisting of hydrogen, a linear, branched, or cyclic, optionally substituted $C_1$-$C_{24}$ alkyl group, an optionally substituted $C_6$-$C_{24}$ (hetero) aryl group, an optionally substituted $C_7$-$C_{24}$ (hetero) arylalkyl group, and an optionally substituted $C_7$-$C_{24}$ alkyl(hetero)aryl group, wherein the alkyl groups, (hetero)aryl groups, (hetero)arylalkyl groups and alkyl(hetero)aryl groups may be substituted with one or more substituents P;

the substituent P is selected from the group consisting of hydrogen; —CH═CH(R¹)₂; —C≡CR¹; halogen; —CN; —NCX; —XCN; —XR¹; —N(R¹)₂; —⁺N(R¹)₃; —CN; —C(X)N(R¹)₂; —C(X)R¹; —C(X)XR¹; —S(O)R¹; —S(O)₂R¹; —S(O)OR¹; —S(O)₂OR¹; —S(O)N(R¹)₂; —S(O)₂N(R¹)₂; —OS(O)R¹; —OS(O)₂R¹; —OS(O)OR¹; —OS(O)₂OR¹; —P(O)(R¹)(OR¹); —P(O)(OR¹)₂; —OP(O)(OR¹)₂; —Si(R¹)₃; —XC(X)R¹; —XC(X)XR¹; —XC(X)N(R¹)₂; —N(R¹)C(X)R¹; —N(R¹)C(X)XR¹; and —N(R¹)C(X)N(R¹)₂; wherein X is oxygen or sulphur and wherein all R¹ substituents are independently selected from the group consisting of hydrogen, $C_1$-$C_{24}$ alkyl groups, $C_6$-$C_{24}$ (hetero)aryl groups, $C_7$-$C_{24}$ alk(hetero)aryl groups, and $C_7$-$C_{24}$ (hetero)arylalkyl groups; and E is a group according to Formula (VII):

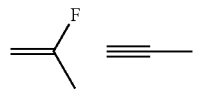

(VII)

wherein F is hydrogen or a linear $C_1$-$C_6$ alkyl group.

2. A process for preparing a functionalized Si/Ge-surface, wherein an unfunctionalized Si/Ge-surface is contacted in the presence of ultraviolet radiation with a $C_2$-$C_{50}$ alkene and/or a $C_2$-$C_{50}$ alkyne, the alkene and/or alkyne being optionally substituted and/or being optionally interrupted by one or more heteroatoms, wherein the unfunctionalized Si/Ge-surface is selected from the group consisting of silicon nitride, silicon carbide, germanium nitride, germanium carbide and strained silicon, wherein the $C_2$-$C_{50}$ alkene and/or a $C_2$-$C_{50}$ alkyne have 6 to 24 carbon atoms according to Formulas (X) and (XI):

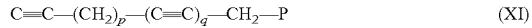

wherein p is in the range of 1 to 7 and q is in the range of 1 to 7, the groups —(CH₂)— and —(C≡C)— optionally occurring in a random sequence, and the substituent P is selected from the group consisting of hydrogen; —CH═CH(R¹)₂; —C≡CR¹; halogen; —CN; —NCX; —XCN; —XR¹; —N(R¹)₂; —⁺N(R¹)₃; —CN; —C(X)N(R¹)₂; —C(X)R¹; —C(X)XR¹; —S(O)R¹; —S(O)₂R¹; —S(O)OR¹; —S(O)₂OR¹; —S(O)N(R¹)₂; —S(O)₂N(R¹)₂; —OS(O)R¹; —OS(O)₂R¹; —OS(O)OR¹; —OS(O)₂OR¹; —P(O)(R¹)(OR¹); —P(O)(OR¹)₂; —OP(O)(OR¹)₂; —Si(R¹)₃; —XC(X)R¹; —XC(X)XR¹; —XC(X)N(R¹)₂; —N(R¹)C(X)R¹; —N(R¹)C(X)XR¹; and —N(R¹)C(X)N(R¹)₂; wherein X is oxygen or sulphur and wherein all R¹ substituents are independently selected from the group consisting of hydrogen, $C_1$-$C_{24}$ alkyl groups, $C_6$-$C_{24}$ (hetero)aryl groups, $C_7$-$C_{24}$ alk(hetero)aryl groups, and $C_7$-$C_{24}$ (hetero)arylalkyl groups.

3. A process for preparing a functionalized Si/Ge-surface, wherein an unfunctionalized Si/Ge-surface is contacted in the presence of ultraviolet radiation with a $C_2$-$C_{50}$ alkene and/or a $C_2$-$C_{50}$ alkyne, the alkene and/or alkyne being optionally substituted and/or being optionally interrupted by one or more heteroatoms, wherein the unfunctionalized Si/Ge-surface is selected from the group consisting of silicon nitride, silicon carbide, germanium nitride, germanium carbide and strained silicon, wherein the $C_2$-$C_{50}$ alkene and/or a $C_2$-$C_{50}$ alkyne are substituted at their co-position with (i) a group according to Formula (IV) and Formula (V):

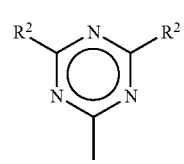

(IV)

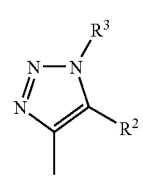

(V)

or tautomers thereof, wherein R² is selected from the group consisting of: hydrogen, —OH, and —NH₂; and wherein R³ is selected from the group consisting of hydrogen, $C_1$-$C_{24}$ alkyl groups, $C_6$-$C_{24}$ (hetero)aryl groups, $C_7$-$C_{24}$ alk(hetero)aryl groups, and $C_7$-$C_{24}$ (hetero)arylalkyl groups;

(ii) ethylene oxide propylene oxide polymers according to the formula —B—C, wherein B is a —[X-D-X]ₙ— group, wherein all X groups are independently selected from the group consisting of —O—, —S— and —N(R¹)— (wherein R¹ is as R³), D represents an (optionally substituted) ethylene group, an (optionally substituted) propylene group, or a mixture thereof (wherein the ethylene groups and propylene groups may be substituted with one or more substituents P), n is in the range of 1-100; C is selected from the group consisting of hydrogen, a linear, branched, or cyclic, optionally substituted $C_1$-$C_{24}$ alkyl group, an optionally substituted $C_6$-$C_{24}$ (hetero)aryl group, an optionally substituted $C_7$-$C_{24}$ (hetero)arylalkyl group, and an optionally substituted $C_7$-$C_{24}$ alkyl(hetero)aryl group, wherein the alkyl groups, (hetero)aryl groups, (hetero)arylalkyl groups and alkyl(hetero)aryl groups may be substituted with one or more substituents P; and the substituent P is selected from the group consisting of hydrogen, —CH═CH(R¹)₂; C≡CR¹; halogen; —CN; —NCX; —XCN; —XR¹; —N(R¹)₂; —⁺N(R¹)₃; —CN; —C(X)N(R¹)₂; —C(X)R¹; —C(X)XR¹; —S(O)R¹; —S(O)₂R¹; —S(O)OR¹, —S(O)₂OR¹; —S(O)N(R¹)₂; —S(O)₂N(R¹)₂; —OS(O)R¹; —OS(O)₂R¹; —OS(O)OR¹; —OS(O)₂OR¹; —P(O)(R¹)(OR¹); —P(O)(OR¹)₂; —OP(O)(OR¹)₂; —Si(R¹)₃; —XC(X)R¹; —XC(X)XR¹; —XC(X)N(R¹)₂; —N(R¹)C(X)R¹; —N(R¹)C(X)XR¹; and —N(R¹)C(X)N(R¹)₂; wherein X is oxygen or sulphur and wherein all R¹ substituents are independently selected from the group consisting of hydrogen, $C_1$-$C_{24}$ alkyl groups, $C_6$-$C_{24}$ (hetero)aryl groups, $C_7$-$C_{24}$ alk(hetero)aryl groups, and $C_7$-$C_{24}$ (hetero)arylalkyl groups, and sugar residues.

* * * * *